United States Patent [19]

Giordano et al.

[11] Patent Number: 5,102,999

[45] Date of Patent: Apr. 7, 1992

[54] PROCESS FOR THE PREPARATION OF AN INTERMEDIATE OF DILTIAZEM

[75] Inventors: Claudio Giordano, Monza; Roberto Casagrande, Bresso, both of Italy

[73] Assignee: Zambon Group S.p.A., Vicenza, Italy

[21] Appl. No.: 612,954

[22] Filed: Nov. 15, 1990

[30] Foreign Application Priority Data

Dec. 6, 1989 [IT] Italy ................ 22637 A/89

[51] Int. Cl.$^5$ ............................................. C07D 281/10
[52] U.S. Cl. ......................................................... 540/491
[58] Field of Search ........................................... 540/491

[56] References Cited

U.S. PATENT DOCUMENTS

| | | | |
|---|---|---|---|
| 3,562,257 | 2/1971 | Kugita et al. | 540/491 |
| 4,416,819 | 11/1983 | Nagao et al. | 540/491 |
| 4,420,628 | 12/1983 | Inoue et al. | 560/17 |
| 4,533,748 | 8/1985 | Manghisi et al. | 540/491 |

FOREIGN PATENT DOCUMENTS

| | | | |
|---|---|---|---|
| 46-8982 | 3/1971 | Japan | 540/491 |
| 60-32779 | 2/1985 | Japan | 540/491 |

OTHER PUBLICATIONS

Chemical Abstracts 99:70782z (1983).
Chemical Abstracts 100:174862f (1984).
Chemical Abstracts 101:211188j (1984).
Chemical Abstracts 101:38486e.
Chemical Abstracts 102:62286f (1985).
Chemical Abstracts 103:87918x.

*Primary Examiner*—Robert T. Bond
*Attorney, Agent, or Firm*—Stevens, Davis, Miller & Mosher

[57] ABSTRACT

A process for the preparation of intermediates useful for the synthesis of Diltiazem consisting in the racemization of (—)-cis-2,3-dihydro-3-hydroxy-2-(4-methoxyphenyl)-1,5-benzothiazepin-4(5H)-one is described.

7 Claims, No Drawings

PROCESS FOR THE PREPARATION OF AN INTERMEDIATE OF DILTIAZEM

The present invention relates to a method for the preparation of intermediates useful for the preparation of benzothiazepines and, more particularly, it relates to a method for the preparation of (±)-cis-2,3-dihydro-3-hydroxy-2-(4-methoxyphenyl)-1,5-benzothiazepin-4(5H)-one of formula

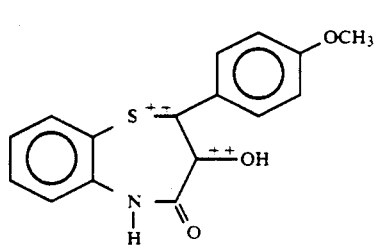

an intermediate useful for the synthesis of Diltiazem. Diltiazem, (+)-(2S,3S)-3-acetoxy-5-[2-(dimethylamino)ethyl]-2,3-dihydro-2-(4-methoxyphenyl)-1,5-benzothiazepin-4(5H)-one (Merck Index, XI Ed., No. 3188, page 505) is a known drug with calcium-antagonist activity described in British patent no. 1,236,467 (Tanabe Seiyaku Co. Ltd.).

Various methods for the preparation of Diltiazem are known in the literature such as for example those described in the above cited British patent No. 1,236,467, in European patent application No. 59,335 (Tanabe Seiyaku Co. Ltd.) and in Japanese patent No. 71/8982 (Tanabe Seiyaku Co. Ltd.).

Most of these methods substantially foresee the following reaction scheme.

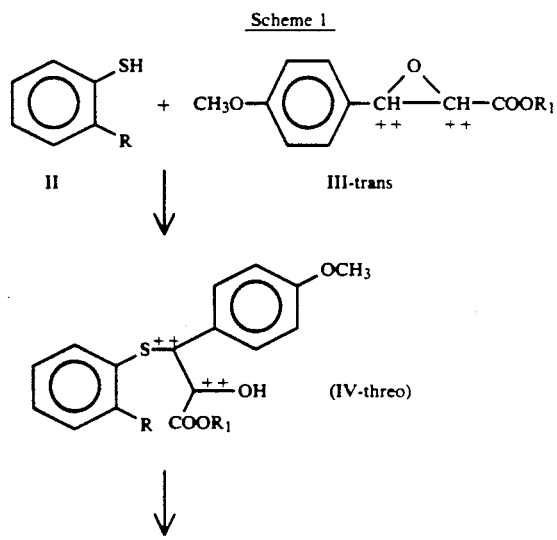

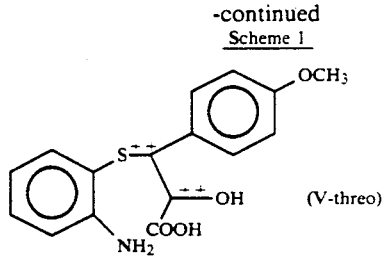

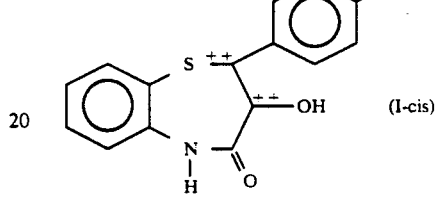

wherein R is an amino or a nitro group; $R_1$ is a lower alkyl and the asterisks mark the asymmetric carbon atoms.

Each of these methods necessarily foresees an optical resolution step, generally at the level of an intermediate of the synthesis, in order to separate the (2S,3S) from the (2R,3R) enantiomer.

In fact, there is known the resolution of the intermediate of formula V by optically active bases such as alpha-phenethylamine described in European patent No. 98,892 (Tanabe Seiyaku Co. Ltd.) and L-lysine described in British patent application No. 2,130,578 (Istituto Luso Farmaco d'Italia S.p.A.).

There is also known the resolution of the intermediate I-cis by suitable chromatographic columns (Japanese patent application No. 59/110686, Higashigawa-Chemical Abstracts 101:211188j) or by chiral macrocyclic polyethers (Japanese patent application No. 59/144776, Higashigawa-Chemical Abstracts 102:62286f).

The resolution at the level of the intermediate V-threo gives the isomer V-(2S,3S) useful for the synthesis of Diltiazem and the isomer V-(2R,3R).

Analogously, the resolution at the level of compound I-cis gives the isomer I-(2S,3S) useful for the synthesis of Diltiazem and the isomer I-(2R,3R).

The isomer I-(2R,3R) can be also prepared by known methods from compound V-(2R,3R).

Therefore, the isomers with (2R,3R) configuration, which are not suitable for the synthesis of Diltiazem, are waste products in the industrial synthesis.

As a consequence, it should be useful to have available a process for the racemization of such compounds in order to recover them for the synthesis of Diltiazem.

We have now found and it is the object of the present invention a process for the conversion of the isomer I-cis with (2R,3R) configuration into a racemic mixture I-cis, that is into a mixture of the (2R,3R) and (2S,3S) enantiomers.

By resolution from this mixture the enantiomer I-(2S,3S) which is used for the synthesis of Diltiazem and the enantiomer I-(2R,3R) which is recycled, are separated.

Alternatively, from the racemic mixture I-cis it is possible to obtain by traditional methods (±)-3-acetoxy-5-[2-(dimethylamino)ethyl]-2,3-dihydro-2-(4-methoxyphenyl)-1,5-benzothiazepin-4(5H)-one from which the (+)-isomer, that is Diltiazem, is separated by known methods (for example according to Japanese patent application No. 58/032872, Nohira-Chemical Abstracts 99:70782z). The process object of the present invention comprises the two following steps:

1. I-cis (2R, 3R) $\xrightarrow{\text{oxidation}}$ (VI)

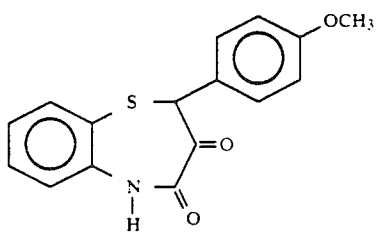

2. VI $\xrightarrow{\text{reduction}}$ I-cis (2R, 3R) + I-cis (2S, 3S).

Reaction 1 is carried out by using a carbonyl compound in the presence of a strong base, in an inert solvent and it gives compound VI wherein the carbon atom bonded to 4-methoxyphenyl group is racemic. Specific examples of the carbonyl compounds which can be used are acetone, 2-butanone, cyclohexanone, benzophenone, fluorenone and benzaldehyde.

Suitable strong bases are metal alkoxides and, in particular potassium or aluminium t.butoxide, potassium amylates. Such alkoxides can be also prepared directly in the reaction environment.

Inert solvents usable in reaction 1 are aprotic solvents, for example tetrahydrofuran, dioxane, toluene, dimethylformamide.

The reaction temperature is not critical within the normal intervals and, preferably, it is between the room value and 100° C. An excess of carbonyl compound with respect to compound I-(2R,3R), preferably 3-6 moles for one mole of I-(2R,3R), is used. Also the base is used in excess, 2-4 moles for one mole of compound I-(2R-3R).

Compound VI is known. The preparation thereof has been described by ring expansion starting from derivatives of 2H-1,4-benzothiazin-3(4H)-one (Japanese patent application No. 58/213764, Hamari Yakuhin Kogy KK-Chemical Abstracts 100:174862f) or by hydrolysis of the compound of formula VII (Japanese patent application No. 60/025982, Tanabe Seiyaku-Chemical Abstracts 103:87918x).

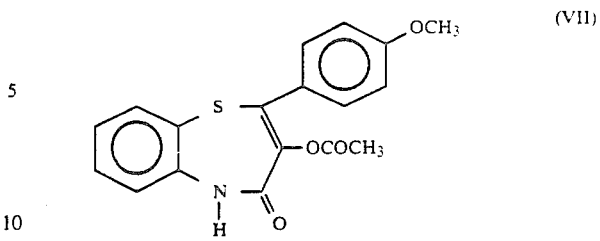

In reaction 2, compound VI is reduced by using a hydride in an inert solvent or by using sodium in alcohol. The reaction yields the racemic mixture of compounds I-cis with high yields and high purity.

Suitable hydrides are borane, aluminum hydrides and NaBH$_4$, the latter being preferred because of its easier industrial applicability. The hydride is preferably used in an equimolar amount or in a slight excess. The suitable inert solvent depends on the specific hydride to be used. In the case of NaBH$_4$, the reaction can be carried out in an ethereal solvent (tetrahydrofuran, dioxane), in an alcohol (methanol, ethanol) optionally in admixture with water. The reduction is preferably carried out at a temperature between −10° C. and 70° C.

As far as we know, reaction 2, which is per se a conventional reaction, has never been carried out on intermediate VI. A similar reaction has been described in Japanese patent application No. 59/020273-Tanabe Seiyaku (Chemical Abstracts 101:38486e) but on an analog of compound VI, that is the N-(2-dimethylaminoethyl)-substituted analog.

Clearly, the starting compound of the process object of the present invention, that is compound I-(2R,3R) can be obtained by a process of resolution of the intermediates I-cis as well as in another way, for example, as above mentioned, by cyclization of intermediate V-(2R,3R), that is (2R,3R)-3-(2-aminophenylthio)-3-(4-methoxyphenyl)-2-hydroxy-propionic acid.

In a preferred practical embodiment, the process object of the present invention comprises the preparation of compound VI by oxidation of compound I-(2R,3R) with a carbonyl compound and potassium t.butoxide in an aprotic inert solvent and the reduction of compound VI with NaBH$_4$ in an inert solvent.

In a more preferred embodiment, the carbonyl compound is selected between benzophenone and fluorenone, the solvent of the oxidation reaction is selected among tetrahydrofuran, dioxane and toluene, the solvent of the reduction reaction is selected among tetrahydrofuran, methanol and ethanol.

In order to better illustrate the present invention, without limiting it, the following examples are now given.

EXAMPLE 1

Into a 50 ml reactor equipped with a magnetic stirrer, a thermometer and a reflux condenser, under nitrogen atmosphere and by heating in an oil bath, tetrahydrofuran (30 ml), (2R,3R)-(−)-cis-2,3-dihydro-3-hydroxy-2-(4-methoxyphenyl)-1,5-benzothiazepin-4(5H)-one (1.5 g; 5 mmol), benzophenone (4.7 g; 26 mmol) and potassium t.butoxide (1.95 g; 16 mmol) were charged under stirring.

The reaction mixture was heated to reflux temperature (70° C.) and the suspension was kept under stirring for 20 hours.

Then, the reaction mixture was poured into a solution of monobasic and dibasic potassium phosphate (50 ml) at pH 7.

Ethyl acetate (30 ml) was added and the phases were separated. The aqueous phase was further extracted with ethyl acetate (30 ml). The collected organic phases were washed with water (10 ml), dried and the solvent was evaporated under reduced pressure.

The obtained crude solid was collected with tetrahydrofuran (20 ml) and sodium borohydride (1.2 g; 31.5 mmol) was added at 15° C. while keeping the solution under stirring.

After an hour, the reaction mixture was poured into a buffer solution (20 ml) at pH 7.

The phases were separated and the aqueous phase was extracted with methylene chloride (20 ml).

A solution was obtained which, by HPLC analysis, resulted to contain a mixture 1:1 of (2S,3S) and (2R,3R)-cis-2,3-dihydro-3-hydroxy-2-(4-methoxyphenyl)-1,5-benzothiazepin-4(5H)-one (1.1 g) with a 70% molar yield with respect to the starting compound.

The solvent was removed from the above solution by evaporation under reduced pressure to give a crude from which the desired racemic mixture (m.p. 168°-170° C.) was isolated by crystallization with methanol.

EXAMPLE 2

Compound (2R,3R)-(−)-cis-2,3-dihydro-3-hydroxy-2-(4-methoxyphenyl)-1,5-benzothiazepin-4(5H)-one (5 g) was oxidized according to the procedure described in example 1.

The reaction crude was chromatographied on silica gel with a mixture of methylene chloride and ethyl acetate (9:1) to give racemic compound VI (4.25 g; 85% yield). In solution, the compound appeared as a mixture of tautomers.

NMR: in CDCl$_3$ (300 MHz) delta 5.45 ppm CHCO; I.R.: C=O stretching 1730 cm$^{-1}$.

Sodium borohydride (0.567 g; 15 mmol) was added at 15° C. under stirring in a minute to a solution of compound VI (14.2 mmol) in methanol (65 ml) and the reaction mixture was kept under stirring for 1 hour at 15° C.

Then, the mixture was poured into a buffer solution of dibasic and monobasic phosphate (100 ml) at pH 7; methanol was removed by distillation under vacuum: then, the mixture was extracted with methylene chloride (2×30 ml).

After drying of the organic extract, the solvent was evaporated under vacuum to give a mixture 1:1 of (2S,3S) and (2R,3R)-cis-2,3-dihydro-3-hydroxy-2-(4-methoxyphenyl)-1,5-benzothiazepin-4(5H)-one (4.15 g; 97% yield; m.p.=168°-170° C.).

EXAMPLE 3

Compound (2R,3R)-(−)-cis-2,3-dihydro-3-hydroxy-2-(4-methoxyphenyl)-1,5-benzothiazepin-4(5H)-one was oxidized to compound VI according to the procedure described in example 1, but benzophenone was substituted by an equimolar amount of fluorenone.

EXAMPLE 4

Compound (2R,3R)-(−)-cis-2,3-dihydro-3-hydroxy-2-(4-methoxyphenyl)-1,5-benzothiazepin-4(5H)-one was oxidized to compound VI according to the procedure described in example 1, but toluene (15 ml) was used as a solvent instead of tetrahydrofuran.

EXAMPLE 5

The present example describes the process carried out by preparing in situ potassium t.butoxide.

Potassium hydride (30 mmol) was added at 15° C. to a solution of t.butyl alcohol (26 mmol) in DMF (30 ml) and the mixture was kept under stirring for 2 hours.

(2R,3R)-(−)-cis-2,3-dihydro-3-hydroxy-2-(4-methoxyphenyl)-1,5-benzothiazepin-4(5H)-one (5 mmol) and benzophenone (26 mmol) were added to the solution of potassium t.butoxide.

Then, the mixture was heated under stirring to 100° C. and it was kept at this temperature under nitrogen and under stirring for 2 hours. After cooling and reduction with NaBH$_4$ as described in example 1 a mixture 1:1 of (2S,3S) and (2R,3R)-cis-2,3-dihydro-3-hydroxy-2-(4-methoxyphenyl)-1,5-benzothiazepin-4(5H)-one was obtained.

What we claim is:

1. A process for the conversion of 2,3-dihydro-3-hydroxy-2-(4-methoxyphenyl)-1,5-benzothiazepin-4(5H)-one with cis (2R,3R) configuration into a mixture of cis (2R,3R) and cis (2S,3S)-2,3-dihydro-3-hydroxy-2-(4-methoxyphenyl)-1,5-benzothiazepin-4(5H)-one comprising the oxidation of the cis (2R,3R) enantiomer with a carbonyl compound selected from the group consisting of acetone, 2-butanone, cyclohexanone, benzophenone, fluorenone and benzaldehyde and a strong base, wherein the base is a metal alkoxide, in an aprotic inert solvent to obtain the compound of formula

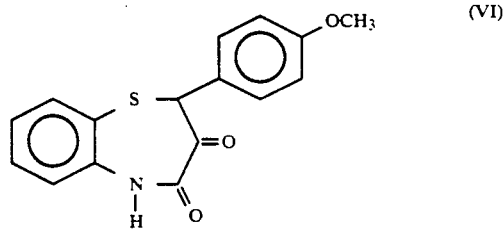

and the reduction thereof with a hydride in an inert solvent or with sodium in alcohol.

2. A process according to claim 1 wherein, in the oxidation step, the strong base is selected from the group consisting of potassium t.butoxide, aluminum t.butoxide and potassium amylates.

3. A process according to claim 1 wherein, in the oxidation step, the aprotic inert solvent is selected from the group consisting of tetrahydrofuran, dioxane, toluene and dimethylformamide.

4. A process according to claim 1 wherein, in the reduction step, the hydride is selected from the group consisting of borane, aluminum hydrides and NaBH$_4$.

5. A process according to claim 1 wherein the reduction step is carried out with a hydride in an inert solvent, and the inert solvent is selected from the group consisting of tetrahydrofuran, methanol, ethanol and mixture thereof with water.

6. A process according to claim 1 wherein the starting compound is prepared by cyclization of (2R,3R)-3-(2-aminophenylthio)-3-(4-methoxyphenyl)-2-hydroxy propionic acid.

7. A process according to claim 1 wherein (2R,3R)-cis-2,3-dihydro-3-hydroxy-2-(4-methoxyphenyl)-1,5-benzothiazepin-4(5H)-one is oxidized to compound VI by reaction with potassium t.butoxide and benzophenone in an aprotic inert solvent and the so obtained compound VI is reduced with NaBH$_4$ in an inert solvent.

* * * * *